United States Patent [19]
Leslie et al.

[11] Patent Number: 6,068,855
[45] Date of Patent: May 30, 2000

[54] PHARMACEUTICAL COMPOSITION CONTAINING A FUSIBLE CARRIER AND METHOD FOR PRODUCING THE SAME

[75] Inventors: Stewart Thomas Leslie, Cambridge; Trevor John Knott, Bishops Stortford; Hasssan Mohammad, Haslingfield; Derek Allan Prater, Milton, all of United Kingdom

[73] Assignee: Euro-Celtique S. A., Luxembourg, Luxembourg

[21] Appl. No.: 08/817,956

[22] PCT Filed: Nov. 3, 1995

[86] PCT No.: PCT/GB95/02579

§ 371 Date: Aug. 18, 1997

§ 102(e) Date: Aug. 18, 1997

[87] PCT Pub. No.: WO96/14059

PCT Pub. Date: May 17, 1996

[30] Foreign Application Priority Data

Nov. 3, 1994 [GB] United Kingdom ................... 9422154

[51] Int. Cl.⁷ ................... A61J 3/02; A61J 3/06; A61K 9/26; B29B 0/00
[52] U.S. Cl. .......... 424/468; 424/451; 424/452; 424/457; 424/464; 424/465; 424/469; 424/489; 424/502
[58] Field of Search ................... 424/451, 452, 424/457, 464, 465, 468, 469, 470, 484, 489, 502; 514/962, 964, 965; 426/516

[56] References Cited

U.S. PATENT DOCUMENTS

| | | | |
|---|---|---|---|
| Re. 33,093 | 10/1989 | Schiraldi et al. | 424/676 |
| 2,738,303 | 3/1956 | Blythe et al. | 167/82 |
| 3,065,143 | 11/1962 | Christenson et al. | |
| 3,652,589 | 3/1972 | Flick et al. | 260/326.5 M |
| 3,830,934 | 8/1974 | Flick et al. | 424/330 |
| 3,845,770 | 11/1974 | Theeuwes et al. | 128/260 |
| 3,880,991 | 4/1975 | Yolles | 424/22 |
| 3,916,889 | 11/1975 | Russel | 128/145.8 |
| 3,950,508 | 4/1976 | Mony et al. | 424/19 |
| 3,965,256 | 6/1976 | Leslie | 424/22 |
| 3,974,157 | 8/1976 | Shetty et al. | 260/247.2 B |
| 4,013,784 | 3/1977 | Speiser | 424/19 |
| 4,063,064 | 12/1977 | Saunders | 219/121 |
| 4,076,798 | 2/1978 | Casey et al. | 424/419 |
| 4,088,864 | 5/1978 | Theuwes et al. | 219/121 LM |
| 4,132,753 | 1/1979 | Blichare et al. | 264/462 |
| 4,173,417 | 11/1979 | Kruder | 366/89 |
| 4,230,687 | 10/1980 | Sair et al. | 424/22 |
| 4,259,314 | 3/1981 | Lowey | 424/19 |
| 4,265,875 | 5/1981 | Byrne et al. | 424/19 |
| 4,292,300 | 9/1981 | Byrne et al. | 424/19 |
| 4,310,483 | 1/1982 | Dorfel et al. | 264/117 |
| 4,343,789 | 8/1982 | Kawata et al. | 424/461 |
| 4,344,431 | 8/1982 | Yolles | 128/260 |
| 4,346,709 | 8/1982 | Schmitt | 128/260 |
| 4,366,172 | 12/1982 | Lednicer | 424/330 |
| 4,374,082 | 2/1983 | Hochschild | 264/129 |
| 4,380,534 | 4/1983 | Fukui et al. | 264/38 |
| 4,389,393 | 6/1983 | Schor et al. | 264/19 |
| 4,406,883 | 9/1983 | Byrne et al. | 424/80 |
| 4,421,736 | 12/1983 | Walters et al. | 424/21 |
| 4,483,847 | 11/1984 | Augart | 424/470 |
| 4,533,562 | 8/1985 | Ikegami et al. | 427/22 |
| 4,613,619 | 9/1986 | Sleigh et al. | 514/546 |
| 4,621,114 | 11/1986 | Watanabe | 524/451 |
| 4,649,042 | 3/1987 | Davis et al. | |
| 4,720,384 | 1/1988 | DiLuccio et al. | |
| 4,762,220 | 8/1988 | Lütke | 198/519 |
| 4,764,378 | 8/1988 | Keith et al. | |
| 4,778,676 | 10/1988 | Yang et al. | 424/79 |
| 4,797,410 | 1/1989 | El-Fakahany | 514/356 |
| 4,801,458 | 1/1989 | Hidaka et al. | 424/443 |
| 4,801,460 | 1/1989 | Goertz et al. | 424/465 |
| 4,806,337 | 2/1989 | Snipes et al. | 71/65 |
| 4,818,450 | 4/1989 | Hall et al. | 264/39 |
| 4,828,836 | 5/1989 | Elger et al. | 424/470 |
| 4,834,984 | 5/1989 | Goldie et al. | 424/488 |
| 4,834,985 | 5/1989 | Elger et al. | 424/488 |
| 4,842,761 | 6/1989 | Rutherford | 252/90 |
| 4,844,907 | 7/1989 | Elger et al. | 424/465 |
| 4,844,909 | 7/1989 | Goldie et al. | 424/480 |
| 4,861,598 | 8/1989 | Oshlack | 424/468 |
| 4,879,108 | 11/1989 | Yang et al. | 424/440 |
| 4,880,585 | 11/1989 | Klimesch et al. | 264/141 |
| 4,880,830 | 11/1989 | Rhodes | 424/470 |
| 4,882,151 | 11/1989 | Yang et al. | 424/440 |
| 4,882,152 | 11/1989 | Yang et al. | 424/440 |
| 4,882,153 | 11/1989 | Yang et al. | 424/440 |
| 4,882,155 | 11/1989 | Yang et al. | 424/440 |
| 4,882,156 | 11/1989 | Yang et al. | 424/440 |
| 4,882,157 | 11/1989 | Yang et al. | 424/440 |
| 4,882,159 | 11/1989 | Yang et al. | 424/440 |
| 4,882,167 | 11/1989 | Yang | 424/468 |
| 4,894,234 | 1/1990 | Sharma et al. | 424/400 |
| 4,917,899 | 4/1990 | Geoghegan et al. | 424/19 |

(List continued on next page.)

FOREIGN PATENT DOCUMENTS

| | | | |
|---|---|---|---|
| WO 8976091 | 6/1992 | Australia | A23L 1/09 |
| 2082573 | 5/1993 | Canada | A61K 47/38 |
| 2131350 | 3/1995 | Canada | A61K 31/135 |
| 2150304 | 12/1995 | Canada | B01J 2/20 |

(List continued on next page.)

OTHER PUBLICATIONS

Thomsen, L. Juul, "Matrix Pellets Prolonged Formulations Prepared by Melt Pelletization", Dept. of Pharm. Royal Danish School of Pharmacy, 1992.

(List continued on next page.)

*Primary Examiner*—Peter H. Harrison
*Attorney, Agent, or Firm*—Davidson, Davidson & Kappel, LLC

[57] ABSTRACT

A process for the manufacture of particles comprises mechanically working a mixture of a drug and a hydrophobic and/or hydrophilic fusible carrier in a high speed mixture so as to form agglomerates, breaking the agglomerates to give controlled release particles and optionally continuing the mechanical working with the optional addition of a low percentage of the carrier or diluent.

25 Claims, No Drawings

U.S. PATENT DOCUMENTS

| | | | |
|---|---|---|---|
| 4,925,675 | 5/1990 | Giannini et al. | 424/78 |
| 4,935,246 | 6/1990 | Ahrens | 424/490 |
| 4,957,681 | 9/1990 | Klimesch et al. | 264/211 |
| 4,959,208 | 9/1990 | Chakrabarti et al. | 424/78 |
| 4,967,486 | 11/1990 | Doelling | 34/1 |
| 4,970,075 | 11/1990 | Oshlack | 424/451 |
| 4,975,284 | 12/1990 | Stead et al. | 424/497 |
| 4,987,136 | 1/1991 | Kreek et al. | |
| 4,990,341 | 2/1991 | Goldie et al. | 424/484 |
| 4,992,100 | 2/1991 | Koepff et al. | 106/125 S |
| 4,994,227 | 2/1991 | Dietz et al. | 264/328.16 |
| 5,007,790 | 4/1991 | Shell | 424/451 |
| 5,023,089 | 6/1991 | Sakamoto et al. | 424/502 |
| 5,026,560 | 6/1991 | Makino et al. | 424/494 |
| 5,030,400 | 7/1991 | Danielson et al. | 264/101 |
| 5,035,509 | 7/1991 | Kruder | 366/89 |
| 5,049,394 | 9/1991 | Howard et al. | 424/490 |
| 5,055,307 | 10/1991 | Tsuru et al. | 424/693 |
| 5,071,646 | 12/1991 | Malkowska et al. | 424/497 |
| 5,073,379 | 12/1991 | Klimesh et al. | 424/467 |
| 5,102,668 | 4/1992 | Eichel et al. | 424/490 |
| 5,126,145 | 6/1992 | Evenstad | 424/465 |
| 5,132,142 | 7/1992 | Jones et al. | 427/196 |
| 5,133,974 | 7/1992 | Paradissis et al. | 424/480 |
| 5,147,593 | 9/1992 | Huttllin | 264/500 |
| 5,162,117 | 11/1992 | Stupak et al. | 424/475 |
| 5,167,964 | 12/1992 | Muhammed et al. | 424/482 |
| 5,169,645 | 12/1992 | Shukla et al. | 424/499 |
| 5,178,868 | 1/1993 | Malmqvist-Granlund et al. | 424/490 |
| 5,183,690 | 2/1993 | Carr et al. | 427/213.31 |
| 5,196,203 | 3/1993 | Boehm | 424/490 |
| 5,202,128 | 4/1993 | Morella et al. | 424/469 |
| 5,204,119 | 4/1993 | Shiobara et al. | 424/469 |
| 5,229,148 | 7/1993 | Copper | 426/5 |
| 5,240,400 | 8/1993 | Fujimoto et al. | 425/310 |
| 5,262,172 | 11/1993 | Sipos | 424/490 |
| 5,266,331 | 11/1993 | Oshlack et al. | 424/468 |
| 5,271,934 | 12/1993 | Goldberg et al. | 424/401 |
| 5,273,758 | 12/1993 | Royce | 424/465 |
| 5,273,760 | 12/1993 | Oshlack et al. | 424/480 |
| 5,283,065 | 2/1994 | Doyan et al. | 424/467 |
| 5,286,493 | 2/1994 | Oshlack et al. | 424/468 |
| 5,290,560 | 3/1994 | Autant et al. | 424/438 |
| 5,292,461 | 3/1994 | Juch et al. | 264/37 |
| 5,296,266 | 3/1994 | Kunugi et al. | 427/213 |
| 5,300,300 | 4/1994 | Egidio et al. | 424/456 |
| 5,321,012 | 6/1994 | Mayer et al. | 514/25 |
| 5,330,766 | 7/1994 | Morella et al. | 424/490 |
| 5,340,581 | 8/1994 | Tseng et al. | 424/401 |
| 5,350,584 | 9/1994 | McClelland et al. | 424/501 |
| 5,354,856 | 10/1994 | Kawashima et al. | 536/127 |
| 5,356,635 | 10/1994 | Raman et al. | 424/484 |
| 5,378,462 | 1/1995 | Boedecker | 424/94.29 |
| 5,378,474 | 1/1995 | Morella | 424/469 |
| 5,380,535 | 1/1995 | Geyer | 424/484 |
| 5,395,626 | 3/1995 | Kotwal et al. | 424/472 |
| 5,403,593 | 4/1995 | Royce | 424/489 |
| 5,443,846 | 8/1995 | Yoshioka et al. | 424/498 |
| 5,453,283 | 9/1995 | Munch et al. | 424/489 |
| 5,456,923 | 10/1995 | Nakamichi | 424/489 |
| 5,472,710 | 12/1995 | Klokkers-Bethke et al. | 424/468 |
| 5,476,528 | 12/1995 | Trimm | 71/21 |
| 5,476,667 | 12/1995 | Kristensen et al. | 424/489 |
| 5,478,577 | 12/1995 | Sackler et al. | 424/489 |
| 5,500,227 | 3/1996 | Oshlack et al. | 424/476 |
| 5,510,114 | 4/1996 | Borella | 424/452 |
| 5,516,205 | 5/1996 | Oda | 366/75 |
| 5,549,912 | 8/1996 | Oshlack | 424/468 |
| 5,552,159 | 9/1996 | Mueller | 424/464 |
| 5,567,439 | 10/1996 | Myers | 424/486 |
| 5,591,452 | 1/1997 | Miller et al. | 424/468 |
| 5,601,842 | 2/1997 | Bartholomaeus | 424/464 |
| 5,807,583 | 9/1998 | Kristensen et al. | 424/489 |
| 5,843,480 | 12/1998 | Miller et al. | 424/484 |
| 5,849,240 | 12/1998 | Miller et al. | 264/460 |
| 5,891,471 | 4/1999 | Miller et al. | 424/468 |
| 5,958,452 | 9/1999 | Oshlack et al. | 424/457 |
| 5,965,161 | 10/1999 | Oshlack et al. | 424/457 |
| 5,965,163 | 10/1999 | Miller et al. | 424/468 |

FOREIGN PATENT DOCUMENTS

| | | | |
|---|---|---|---|
| 0032004 | 12/1980 | European Pat. Off. | A61K 9/22 |
| 0097523 | 8/1983 | European Pat. Off. | A61K 9/26 |
| 0043254 | 5/1984 | European Pat. Off. | A61K 9/26 |
| 0108218 | 5/1984 | European Pat. Off. | A61K 9/22 |
| 0147780 | 12/1984 | European Pat. Off. | A61K 9/32 |
| 0152379 | 8/1985 | European Pat. Off. | A61K 9/50 |
| 0214735 | 7/1986 | European Pat. Off. | A61K 9/22 |
| 0189861 | 8/1986 | European Pat. Off. | A61K 47/00 |
| 0204596 | 12/1986 | European Pat. Off. | A61K 9/22 |
| 0248548 | 5/1987 | European Pat. Off. | A61K 9/22 |
| 0249347 A2 | 5/1987 | European Pat. Off. | A61K 31/485 |
| 0251459 | 5/1987 | European Pat. Off. | A61K 9/22 |
| 0253104 | 6/1987 | European Pat. Off. | A61K 9/00 |
| 0254978 | 2/1988 | European Pat. Off. | A61K 9/22 |
| 0256127 | 2/1988 | European Pat. Off. | C12N 9/00 |
| 0267702 | 5/1988 | European Pat. Off. | A61K 9/14 |
| 0271193 | 6/1988 | European Pat. Off. | A61K 31/485 |
| 0275834 | 7/1988 | European Pat. Off. | A61K 9/20 |
| 0021129 | 9/1988 | European Pat. Off. | A61K 9/16 |
| 0295212 | 12/1988 | European Pat. Off. | A61K 47/00 |
| 0327295 | 8/1989 | European Pat. Off. | A61K 9/52 |
| 0068450 | 1/1990 | European Pat. Off. | A61K 9/20 |
| 0351580 | 1/1990 | European Pat. Off. | A61K 9/22 |
| 0377518 | 1/1990 | European Pat. Off. | A61K 9/52 |
| 0354345 | 2/1990 | European Pat. Off. | C09H 9/04 |
| 0358107 | 3/1990 | European Pat. Off. | A61K 9/20 |
| 0360562 | 3/1990 | European Pat. Off. | |
| 0361680 | 4/1990 | European Pat. Off. | A61K 9/46 |
| 0361910 | 4/1990 | European Pat. Off. | A61K 9/16 |
| 0368247 | 5/1990 | European Pat. Off. | A61K 9/26 |
| 0375063 | 6/1990 | European Pat. Off. | A61K 9/18 |
| 0377517 | 7/1990 | European Pat. Off. | A61K 31/52 |
| 0298355 | 11/1990 | European Pat. Off. | A61K 9/50 |
| 0415693 | 3/1991 | European Pat. Off. | A61K 37/02 |
| 0430287 | 6/1991 | European Pat. Off. | A61K 9/54 |
| 0463833 | 6/1991 | European Pat. Off. | A61K 9/26 |
| 0241615 | 9/1991 | European Pat. Off. | A61K 9/22 |
| 0452145 | 10/1991 | European Pat. Off. | A61K 9/14 |
| 0239983 | 11/1991 | European Pat. Off. | A61J 3/06 |
| 0465338 | 1/1992 | European Pat. Off. | A61K 9/16 |
| 0481600 | 4/1992 | European Pat. Off. | A61L 15/28 |
| 0531611 | 4/1992 | European Pat. Off. | A61K 9/02 |
| 0535841 | 9/1992 | European Pat. Off. | A61K 31/485 |
| 0320480 | 11/1992 | European Pat. Off. | B01F 5/22 |
| 0526862 | 2/1993 | European Pat. Off. | A61K 9/20 |
| 0533297 | 3/1993 | European Pat. Off. | A61K 9/46 |
| 0534628 | 3/1993 | European Pat. Off. | A61K 31/485 |
| 0546676 | 6/1993 | European Pat. Off. | A61K 31/60 |
| 0580860 | 2/1994 | European Pat. Off. | |
| 0582380 | 2/1994 | European Pat. Off. | B01J 2/16 |
| 0595311 | 5/1994 | European Pat. Off. | A61K 31/44 |
| 0249347 B1 | 6/1994 | European Pat. Off. | A61K 31/485 |
| 0636370 | 2/1995 | European Pat. Off. | A61K 31/485 |
| 0491238 | 3/1995 | European Pat. Off. | B30B 11/22 |
| 0609961 | 8/1995 | European Pat. Off. | A61K 31/485 |
| 0665010 | 8/1995 | European Pat. Off. | A61K 9/26 |
| 0205282 | 9/1995 | European Pat. Off. | A61K 9/22 |
| 0624366 | 5/1996 | European Pat. Off. | A61K 31/485 |
| 2273512 | 1/1976 | France | A61J 3/06 |
| 2273584 | 1/1976 | France | B01J 2/10 |
| 2642420 | 3/1990 | France | C07C 55/10 |

| | | | |
|---|---|---|---|
| 2439538 | 3/1976 | Germany | A61K 9/22 |
| 3602370 | 8/1987 | Germany | A61K 45/06 |
| 3623193 | 1/1988 | Germany | A61K 31/205 |
| 4329794 | 3/1995 | Germany | A61K 31/135 |
| 52-57315 | 5/1977 | Japan | A61K 9/22 |
| 2223513 | 9/1990 | Japan | A61K 9/10 |
| 2223533 | 9/1990 | Japan | A61K 47/14 |
| 0997399 | 4/1964 | United Kingdom . | |
| 1405088 | 6/1971 | United Kingdom | A61K 9/26 |
| 1504553 | 3/1978 | United Kingdom | A61K 47/00 |
| 1513166 | 6/1978 | United Kingdom | B29B 1/02 |
| 2030861 | 4/1980 | United Kingdom | A61J 3/08 |
| 2111386 | 12/1982 | United Kingdom | A61K 9/20 |
| 2117239 | 3/1983 | United Kingdom | A61K 9/20 |
| 2053681 | 4/1984 | United Kingdom | A61K 9/22 |
| 2196848 | 5/1988 | United Kingdom | A61K 9/22 |
| 2207355 | 1/1991 | United Kingdom | A61M 31/00 |
| 2246514 | 2/1992 | United Kingdom | A61K 9/16 |
| 2281204 | 3/1995 | United Kingdom | A61K 9/16 |
| 2284760 | 6/1995 | United Kingdom | A61K 9/16 |
| WO9119484 | 12/1991 | WIPO | A61K 9/16 |
| WO9119485 | 12/1991 | WIPO | A61K 9/16 |
| WO9201446 | 2/1992 | WIPO | A61K 9/50 |
| WO9202209 | 2/1992 | WIPO | A61K 9/22 |
| 92/06679 | 4/1992 | WIPO . | |
| WO9205774 | 4/1992 | WIPO | A61K 9/18 |
| WO9206679 | 4/1992 | WIPO | A61K 9/16 |
| WO 9218106 | 10/1992 | WIPO | A61K 9/14 |
| WO9222283 | 12/1992 | WIPO | A61K 9/02 |
| WO9300063 | 1/1993 | WIPO | A61J 3/00 |
| WO9300076 | 1/1993 | WIPO | A61K 9/51 |
| WO9304675 | 3/1993 | WIPO | A61K 31/16 |
| WO9307859 | 4/1993 | WIPO | A61K 9/16 |
| WO9307861 | 4/1993 | WIPO | A61K 9/50 |
| WO9310765 | 6/1993 | WIPO | A61K 9/22 |
| 93/18753 | 9/1993 | WIPO . | |
| WO9317667 | 9/1993 | WIPO | A61K 9/16 |
| WO9318753 | 9/1993 | WIPO | A61K 9/16 |
| WO9324110 | 12/1993 | WIPO | A61K 9/20 |
| WO9403160 | 2/1994 | WIPO | A61K 9/32 |
| WO9403161 | 2/1994 | WIPO | A61K 9/52 |
| WO9405262 | 3/1994 | WIPO | A61K 9/16 |
| WO9408568 | 4/1994 | WIPO | A61K 9/26 |
| WO9422431 | 10/1994 | WIPO | A61K 9/20 |
| WO9423698 | 10/1994 | WIPO | A61K 9/14 |
| WO9423700 | 10/1994 | WIPO | A61K 9/16 |
| WO9514460 | 6/1995 | WIPO | A61K 9/14 |
| 9614059 | 5/1996 | WIPO . | |

OTHER PUBLICATIONS

Thomsen, L. Juul, et al., "Prolonged Release Matrix Pellets Prepared by Melt Pelletization I. Process Variables", Drug Development and Instrial Pharmacy, vol. 19, No. 15, pp. 1867–1887 (1993).

Thomsen, L. Juul, et al., "Prolonged Release Matrix Pellets Prepared by Melt Pelletization II. Hydrophobic Substances as Meltable Binders", Drug Development and Industrial Pharmacy, vol. 20, No. 7, pp. 1179–1197 (1994).

Thomsen, L. Juul, "Utilizing melt pelletization technique for the preparation of prolonged release products", Pelletization, (material elaborated by assistant prof. Lars Juul Thomsen, Department of Pharmaceutics, Royal Danish School of Pharmacy for the Die course "Pelletization Technology", Nov. 1992, 106 pags plus 3 appendices.

Thomsen, L. Juul, "Prolonged Release Matrix Pellets Prepared by Melt Pelletization. Part IV: Drug Conent, Drug Particle Size, and Binder Composition", Pharmaceutical Technology Europa, pp. 19–22 (Oct. 1994).

G.M. Crass et al., "Sustained and Controlled Release Drug Delivery Systems", Modern Pharmaceutics, 2nd Edition, pp. 635–671, 1990.

N. Follonier et al., "Evaluation of Hot–Melt Extrusion as a New Technique for the Production of Polymer–Based Pellets for Sustained Release Capsules Containng High Loadings of Freely Soluble Drugs", Drug Dev. and Indus. Pharm., vol. 20, No. 8, pp. 1323–1339, 1994.

Sustained Release Medications, Noyes Data Corp., 1980.

M.A. Longer, "Sustained–Release Drug Delivery Systems", Remington's Pharm. Scie., 18th Edition, pp. 1676–1693, 1990.

M. Zahirul I. Khan, "Recent Trends and Progress in Sustained or Controlled Oral Delivery of Some Water Soluble Drugs: Morphine Salts, Diltiazem and Captopril", Drug Devl. and Indus. Pharm., vol. 21, No. 9, pp. 1037–1070, 1995.

J.P. Skelly, Scale–up of Immediate Release Oral Solid Dosage Forms, AAPS/FDA Workshop Committee, Pharmaceutical Technology, pp. 68–74, Apr. 1995.

SK Baveja et al., Int. J. Pharmaceutics, 41, (1988) pp. 55–62.

Formulating for Controlled Release with Methocel® Premium Cellulose Ethers,The Dow Chemical Company, 1989.

M S Vasquez et al., Drug Dev. & Ind. Pharmacy, 18 (11&12), pp. 1355–1378 (1992).

L W S Cheong et al., Pharm. Res 9 (11) pp. 1510–1514 (1992).

Derwent WPI C92–138727 Abstract JP 04/217 925 of 07.08.92.

Hunt et al., Clin. Ther., vol. 13, No. 4, pp. 482–488, 1990.

Methocel, Colorcon Technical Information.

DA Alderman, Int. J. Pharm. Tech. and Prod. Mfr., 5(3) pp. 1–9, 1984.

HE Huber et al., J. Pharm. Sci. 55 (9) Sep. 1966, pp. 974–976.

Lin SY et al., Current Therapeutic Research 52 (3), pp. 486–492, Sep., 1992.

Aqualon Technical Information Bulletin VC–585, 1991.

P Colombo, Advanced Drug Delivery Reviews, 11 (1993) pp. 37–57.

KV Ranga Rao et al., Int. J. Pharmaceutics, 48 (1988) pp. 1–13.

JE Hogan, Drug Dev. & Ind. Pharmacy, 15 (6 & 7), pp. 975–999 (1989).

JL Ford et al., Int. J. Pharmaceutics, 24 (1985) pp. 327–338.

PB Daly et al. Int. J. Pharmaceutics, 18 (1984) pp. 201–205.

H Lapidus et al., J. Pharm. Sci., 55(8), Aug. 1966, pp. 840–843.

H Lapidus et al., J. Pharm. Sci., 57(8), Aug. 1968, pp. 1292–1301.

Advertisement, MS Contin™ 1986, 1987 The Purdue Frederick Company.

Carstensen, J.T., "Pharmaceutical Principles of Solid Dosage Farms", Ch. 8 & 14, Technomic Publishing, Lancastor, P.A., 1993.

E.M.G. van Bommel, "Production and Evaluation of In Vitro Release Characteristics of Spherical Grandient Matrix Systems", Acta Phar., Technol., 3b (2), pp. 74–78, 1990.

Frank W. Goodhart et al., Design and Use of a Laboratory Extruder for Pharmaceutical Granulations, Journal of Pharm. Scien., 62(1), pp. 133–136 (Jan. 1973).

Publication, KEX, Twin Screw Compounding Extruder, (Oct. 1989).

Derwent Abstract DE 2553026.

Derwent Abstract of JP 62040277.

Derwent Abstract of JP58109411.

Nicolas Follonier et al., "Various Ways of Modulating the Release of Diltiazem Hydrochloride from Hot–melt Extruded Sustained Release Pellets Prepared Using Polymeric Materials", *Journal of Controlled Release*, 36, pp. 243–250 (1995).

Nicolas Follonier et al., Hot–Melt Extruded Pellets for the Sustained Release of Highly Dosed Soluble Drugs, Proced, Intern. Symp. Control. Rel. Bioact.Mater., 18(1991), pp. 578–579.

Alan Royce et al., "Alternative Granulation Technique: Melt Granulation", *Drug Development and Industrial Pharmacy*, 22 (9 & 10), pp. 917–924 (1996).

Jerry March, "Addition to Carbon–Hetero Multiple Bonds", Advanced Organic Chemistry, 2nd Ed., pp. 812–823.

F. Brandstetter et al., "Neue Polymer–Schutzgruppe in Der Oligonucleotidsynthese, 2–Hydroxyathylphenylthioather Von Polyathylenglykol", Tetrahedron Letters No. 31, pp. 2705–2708, 1974.

Kaiko et al. "A single dose study of the effect of food ingestion and timing of dose administration on the pharmacokinetic profile of 30 mg sustained–release morphine sulfate tablets", *Current Therapeutic Research*, pp. 869–878, vol. 47, No. 5, May 1990.

Kaiko et al. "Controlled–release morphine bioavailability (MS Contin® tablets) in the presence and absence of food" *The Hospice Journal*, pp. 17–30, vol. 6(4),1990.

Gourlay, et al., "The reproducibility of oral morphine from solution under fed and fasted conditions", *Journal of Pain and Sympton Management*, pp. 431–436, vol. 6, No. 7, Oct. 1991.

Gourlay et al., "Influence of a high–fat meal on the absorption of morphine from oral solutions", *Clin Pharmacol. Ther.*, PP. 403–468, Oct. 1989.

R. Kinget et al., "Preparation and Properties of Granulates Containing Solid Dispersions", Acta Phar. Tech., vol. 31, No.2, 1985, pp. 57–62.

M. J. Jozwiakowski et al., "Characterization of a Hot–Melt Fluid Bed Coating Process for Fine Granules", Pharm. Resear., vol. 7, No. 11, 1990, pp. 1119–1124.

B. Evrard et al., "Melt Granulation With a New Laboratory High–Shear Mixer", Laboratoire de Pharmacie Galenique, Institut de Pharmacie, (No Date).

M. Niskanen et al., "Pelletization in a Centrifugal Granulator, Part I: Effects of Binder–Solution Concentration", Pharm. Tech. Int'l, Oct. 1990, pp. 22–38.

L. Lachman et al., "The Theory and Practice of Industrial Pharmacy", p. 315, Lea & Febiger, Phi. 1976.

FDA Guide to Inspections of Oral Solid Dosage Forms Pre/Post Approval Issues for Development and Validation, Jan. 1994.

T. Schaefer et al. "Melt Pelletization in a High Shear Mixer I Effects of Process variables and Binder", Acta Pharm. Nord. vol. 4, No.3, pp. 133–140, 1992.

T. Schaefer et al. "Melt Pelletization in a High Shear Mixer II Power Consumption and Granule Growth", Acta Pharm. Nord. vol. 4, No.3, pp. 141–148, 1992.

T. Schaefer, et al., "Melt Granulation in a Laboratory Scale High Shear Mixer", Drug Dev. and Indust. Phar., vol. 16, No. 8, pp. 1249–1277, 1990.

El–Shanawany, S., "Sustained Release of Nitrofurantion From Inert Wax Matrixes", J. Controlled Release, vol. 28, No. 1, issued 1993, pp. 11–19.

P. Flanders, et al., "The Controlled of Drug Releases From Conventional Melt Granulation Matrices", Drug Dev. and Industrial Pharm., vol. 13, No. 6, pp. 1001–1022, 1987.

McTaggart, C.M., et al., "The Evaluation of Formulation and Processing Conditions of a Melt Granulation Process", Int. J. Pharm., vol. 19, No. 2, Issued 1984, pp. 139–148.

PHARMACEUTICAL COMPOSITION CONTAINING A FUSIBLE CARRIER AND METHOD FOR PRODUCING THE SAME

This application is a 371 of PCT GB95/02579.

BACKGROUND AND SUMMARY OF THE INVENTION

The present invention relates generally to a method of manufacturing pharmaceutical dosage forms, for human or veterinary use, preferably sustained release particles, such particles having diameters ranging from 0.1 to 3.0 mm. Such particles may contain analgesics, such as morphine, or other active ingredients. The present invention also relates to dosage forms obtained by processing of the aforesaid particles, such as tablets, suppositories or pessaries.

In our co-pending British Patent Application No. 9404928.5 we describe a process for the manufacture of particles, preferably sustained release particles, which comprises (a) mechanically working in a high-shear mixer, a mixture of a particulate drug and a particulate, hydrophobic and/or hydrophilic fusible carrier or diluent having a melting point from 35 to 150° C. and optionally a release control component comprising a water-soluble fusible material or a particulate, soluble or insoluble organic or inorganic material, at a speed and energy input which allows the carrier or diluent to melt or soften whereby it forms agglomerates;

(b) breaking down the agglomerates to give controlled release particles; and optionally (c) continuing mechanically working optionally with the addition of a low percentage of the carrier or diluent; and optionally (d) repeating steps (c) and possibly (b) one or more times.

DETAILED DESCRIPTION OF THE INVENTION

We have now found that satisfactory results may also be obtained if, instead of classifying the agglomerated material in stage b) the material from stage a) is formed into extrudates of predetermined size, and in preferred embodiments, higher yields and/or higher drug loadings, and greater uniformity of size, than in the earlier process first mentioned above still with satisfactory controlled release properties may be achieved.

The present invention thus includes in one aspect a process for the manufacture of particles, preferably sustained release particles, which comprises:

(a) mechanically working in a high-shear mixer, a mixture of a particulate drug and a particulate, hydrophobic and/or hydrophilic fusible carrier or diluent having a melting point from 35 to 150° C. and optionally a release control component comprising a water soluble fusible material or a particulate, soluble or insoluble, organic or inorganic material, at a speed and energy input which allows the carrier or diluent to melt or soften, whereby it forms agglomerates; and then (b) extruding the resulting material.

The extrusion may be carried out so as to form a rod like extrudate which may be cut or moulded to form unit dosage forms e.g. tablets or suppositories, directly.

Preferably the extrusion is through a plurality of orifices and the extrudate is formed into pieces. In more preferred embodiments the extrusion is through a plurality of small orifices e.g. about 0.25 mm to 1.5 mm e.g. 0.5 mm or 1.0 mm diameter and the extrudate is formed into short lengths of e.g. 0.5 to 1.5 mm e.g. 1.0 mm, suitably by cutting.

A preferred process according to the invention comprises the further steps, (c) of continuing mechanically working the pieces formed from the extrudate, optionally with a further addition of a low percentage of the carrier or diluent; and (d) optionally repeating step (c) and possibly (b) one or more times e.g. up to five times.

Extrusion and forming into short lengths by cutting may be carried out using e.g. an Alexanderwerk, Caleva or Nica machine.

Extrusion operations are well known in the formulation field and are described, for example in Pharmaceutical Dosage forms, Volume 2, Ed. Lieberman and Lachman, Marcel Dehker Inc, New York and Basel.

This process is capable of giving a high yield, generally greater than 85%, and preferably greater than 90% of particles in a desired size range, with a desired in vitro release rate and, uniformity of release rate.

The resulting particles may be sieved to eliminate any oversized or undersized material then formed into the desired dosage units by, for example, encapsulation into hard gelatin capsules containing the required dose of the active substance or by tabletting, filling into sachets or moulding into suppositories, pessaries or forming into other suitable dosage forms.

The drug may be water soluble or water insoluble. Water soluble drugs will usually be used in amounts giving for example a loading of up to about 90% w/w in the resulting particles; water insoluble drugs may be used in higher amounts eg. up to 99% w/w of the resulting particles; Examples of water soluble drugs which can be used in the method of the invention are morphine, hydromorphone, diltiazem, diamorphine and tramadol and pharmaceutically acceptable salts thereof; examples of water insoluble drugs which can be used in the process of the invention are naproxen, ibuprofen, indomethacin and nifedipine.

Among the active ingredient which can be used in the process of the invention are the following;

Analgesics and Antiinflammatories

Dihydrocodeine, Hydromorphone, Morphine, Diamorphine, Fentanyl, Alflentanil, Sufentanyl, Pentazocine, Buprenorphine, Nefopam, Dextropropoxyphene, Flupirtine, Tramadol, Oxycodone, Metamizol, Propyphenazone, Phenazone, Nifenazone, Paracetamol, Phenylbutazone, Oxyphenbutazone, Mofebutazone, Acetyl salicylic acid, Diflunisal, Flurbiprofen, Ibuprofen, Diclofenac, Ketoprofen, Indomethacin, Naproxen, Meptazinol, Methadone, Pethidine, Hydrocodone, Meloxicam, Fenbufen, Mefenamic acid, Piroxicam, Tenoxicam, Azapropazone, Codeine, Antiallergics Pheniramine, Dimethindene, Terfenadine, Astemizole, Tritoqualine, Loratadine, Doxylamine, Mequitazine, Dexchlorpheniramine, Triprolidine, Oxatomide, Antihypertensive Clonidine, Moxonidine, Methyldopa, Doxazosin, Prazosin, Urapidil, Terazosin, Minoxidil, Dihydralazin, Deserpidine, Acebutalol, Alprenolol, Atenolol, Metoprolol, Bupranolol, Penbutolol, Propranolol, Esmolol, Bisoprolol, Ciliprolol, Sotalol, Metipranolol, Nadolol, Oxprenolol, Nifedipine, Nicadipine, Verapamil, Diltiazem, Felodipine, Nimodipine, Flunarizine, Quinapril, Lisinopril, Captopril, Ramipril, Fosinopril, Cilazapril, Enalapril, Antibiotics Democlocycline, Doxycycline, Lymecycline, Minocycline, Oxytetracycline, Tetracycline, Sulfametopyrazine, Ofloxacin, Ciproflaxacin, Aerosoxacin, Amoxycillin, Ampicillin, Becampicillin, Piperacillin, Pivampicillin, Cloxacillin, Penicillin V, Flucloxacillin, Erthromycin, Metronidazole, Clindamycin, Trimethoprim, Neomycin, Cefaclor, Cefadroxil, Cefixime, Cefpodoxime, Cefuroxine, Cephalexin, Cefradine.

Bronchodilator/Anti-Asthmatic

Pirbuterol, Orciprenaline, Terbutaline, Fenoterol, Clenbuterol, Salbutamol, Procaterol, Theophylline, Cholintheophyllinate, Theophylline-ethylenediamine, Ketofen, Antiarrhythmics Viquidil, Procainamide, Mexiletine, Tocainide, Propafenone, Ipratropium, Centrally Acting Substances Amantadine, Levodopa, Biperiden, Benzotropine, Bromocriptine, Procyclidine, Moclobemide, Tranylcypromide, Clomipramine, Maprotiline, Doxepin, Opipramol, Amitriptyline, Desipramine, Imipramine, Fluroxamin, Fluoxetin, Paroxetine, Trazodone, Viloxazine, Fluphenazine, Perphenazine, Promethazine, Thioridazine, Triflupromazine, Prothipendyl, Tiotixene, Chlorprothixene, Haloperidol, Pipamperone, Pimozide, Sulpiride, Fenethylline, Methylphenildat, Trifluoperazine, Thioridazine, Oxazepam, Lorazepam, Bromoazepam, Alprazolam, Diazepam, Clobazam, Buspirone, Piracetam, Cytostatics and Metastasis Inhibitors Melfalan, Cyclophosphamide, Trofosfamide, Chlorambucil, Lomustine, Busulfan, Prednimustine, Fluorouracil, Methotrexate, Mercaptopurine, Thioguanin, Hydroxycarbamide, Altretamine, Procarbazine.

Anti-Migraine

Lisuride, Methysergide, Dihydroergotamine, Ergotamine, Pizotifen,

Gastrointestinal

Cimetidine, Famotidine, Ranitidine, Roxatidine, Pirenzipine, Omeprazole, Misoprostol, Proglumide, Cisapride, Bromopride, Metoclopramide, Oral Antidiabetics Tobutamide, Glibenclamide, Glipizide, Gliquidone, Gliboruride, Tolazamide, Acarbose and the pharmaceutically active salts or esters of the above and combinations of two or more of the above or salts or esters thereof.

The hydrolysis of drugs constitutes the most frequent, and perhaps therefore the most important, route of drug decomposition. Analysis of a collection of stability data in Connors K A, Amidon G L, Stella V J, Chemical stability of pharmaceuticals. A handbook for pharmacists, 2nd ed. New York: John Wiley & Sons, 1986, a standard text, shows that over 70% of the drugs studied undergo hydrolytic degradation reactions. Of these, 61.4% can be classed as reactions of carboxylic acid derivatives (esters, amides, thiol esters, lactams, imides), 20% of carbonyl derivatives (imines, oximes), 14.3% of nucleophilic displacements, and 4.3% of phosphoric acid derivatives. Cephalosporins, penicillins and barbituates are particularly susceptible drug classes.

The process of the invention may advantageously be used for preparing dosage forms containing active substances as mentioned above which are unstable in the presence of water, e.g. diamorphine. Thus stable formulations of such drugs having normal or controlled release characteristics can be obtained in accordance with the invention.

In a preferred method according to the invention morphine sulphate, or other water soluble drug, e.g. tramadol, is used in an amount which results in particles containing e.g. between <1% and 90%, especially between about 45% and about 85% e.g. 75 w/w active ingredient for a high dose product and e.g. <1 and 45% for a low dose product.

In the method of the invention preferably all the drug is added in step (a) together with a major portion of the hydrophobic or hydrophilic fusible carrier or diluent used. Preferably the amount of fusible carrier or diluent added in step (a) is between e.g. 10% and <99% w/w of the total amount of ingredients added in the entire manufacturing operation.

In step (c) the amount of optional additional fusible carrier or diluent added is preferably between 5% and 75% w/w of the total amount of ingredients added. The additional material may be added stepwise.

Stage (a) of the process may be carried out in conventional high-shear mixers with a standard stainless steel interior, e.g. a Collette Vactron 75 or equivalent mixer. The mixture is processed until a bed temperature above 40° C. is achieved and the resulting mixture acquires a cohesive granular texture, with particle sizes ranging from about 1–3 mm to fine powder in the case of non-aggregated original material. Such material, in the case of the embodiments described below, has the appearance of agglomerates which upon cooling below 40° C. have structural integrity and resistance to crushing between the fingers. At this stage the agglomerates are of an irregular size, shape and appearance. The resulting mass is then extruded as described above.

In one preferred form of the process of the invention processing of the extruded materials is continued, until the hydrophobic and/or hydrophilic fusible carrier or diluent materials used begin to soften or melt and additional hydrophobic and/or hydrophilic fusible carrier or diluent material is then added. Mixing is continued until the mixture has been transformed into particles of the desired predetermined size range.

In order to ensure uniform energy input into the ingredients in the high speed mixer it is preferred to supply at least part of the energy by means of microwave energy.

Energy may also be delivered through other means such as by a heating jacket or via the mixer impeller and chopper blades.

After the particles have been formed they are sieved to remove any over or undersized material and then cooled or allowed to cool.

The resulting particles may be used to prepare dosage units e.g. tablets or capsules in manners known per se.

We have found that by suitable selection of the materials used in forming the particles and in the tabletting and the proportions in which they are used, enables a significant degree of control in the ultimate dissolution and release rates of the active ingredients from the compressed tablets.

Suitable substances for use as hydrophobic carrier or diluent materials are natural or synthetic waxes or oils, for example hydrogenated vegetable oil, hydrogenated castor oil, beeswax, carnauba wax, microcrystalline wax and glycerol monostearate, and suitably have melting points of from 35 to 150° C., preferably 45 to 90° C.

Suitable substances for use as hydrophillic carrier or diluent are Polyethylene glycols (PEGs) of various molecular weights e.g. 1,000 to 20,000, preferably 4,000 to 10,000.

The optionally added release control component when a water soluble, fusible material may be a PEG of appropriate molecular weight; suitable particulate inorganic and organic materials are dicalcium phosphate, colloidal anhydrous silica, calcium sulphate, talc, lactose, poloxamers, microcrystalline cellulose, starch, hydroxy propylcellulose, hydroxy propylmethyl cellulose.

In this process of the invention the temperature of the mixing bowl throughout the mechanical working is chosen so as to avoid excessive adhesion, suitably to minimise adhesion of the material to the walls of the bowl. To minimise adhesion we have generally found that the temperature should be neither too high nor too low with respect to the melting temperature of the material and it can be readily optimised to avoid the problems mentioned above. For example in the processes described below in the Examples a bowl temperature of approximately 50–60° C. has been found to be satisfactory and avoids adhesion to the bowl. It is not possible to generalise as to the appropriate temperature or period for the mechanical working for any particular mixture to be processed. However, in practice, it is a matter of simple experimentation and observations to establish a suitable temperature and processing time for a particular mixture under consideration.

To produce tablets in accordance with the invention, particles produced as described above may be mixed or blended with the desired excipient(s), if any, using conventional procedures e.g. using a Y-Cone or bin-blender and the resulting mixture compressed according to conventional tabletting procedure using a suitably sized tabletting tooling. Tablets can be produced using conventional tabletting machines, and in the embodiments described below were produced on standards single punch F3 Manesty machine or Kilian RLE15 rotary tablet machine.

Generally speaking we find that even with highly water soluble active agents such as salts of morphine or tramadol, tablets formed by compression according to standard methods give very low in vitro release rates of the active ingredient e.g. corresponding to release over a period of greater than 24 hours, say more than 36. We have found that the in vitro release profile can be adjusted in a number of ways. For instance in the case of water soluble drugs a higher loading of the drug will be associated with increased release rates; the use of larger proportions of the water soluble fusible material in the particles or surface active agent in the tabletting formulation will also be associated with a higher release rate of the active ingredient: Thus, by controlling the relative amounts of these ingredients it is possible to adjust the release profile of the active ingredient, whether this be water soluble or water insoluble.

In order that the invention may be well understood the following examples are given by way of illustration only.

EXAMPLE 700 g of finely powdered morphine sulphate and 220 g of finely powdered hydrogenated vegetable oil were placed in the bowl of a 10 liter capacity Collette Vactron Mixer (or equivalent) equipped with variable speed mixing and granulating blades. The ingredients were mixed at about 425 rpm with the jacket temperature at 55° C. to 65° C., until the contents of the bowl are agglomerated.

The mass is extruded through 1 mm holes of an Alexanderwerk extruder equipped with a cutting blade located so as to cut the extrudate into approximately 1.0 mm length pieces.

The short lengths of extrudate are collected and returned to the warm bowl of the mixer and operation of the mixture is recommenced. After the extrudates become generally rounded, a further 80 gm of finely divided hydrogenated vegetable oil is added to the bowl and mixing is continued for 3 minutes when the extrudates are generally spherical.

The spherical particles are removed from the bowl, allowed to cool and are then sieved to isolate the sieve fraction 0.5 to 2.0 mm.

The release rates of the sieved particles are then assessed by modified Ph. Eur. Basket method at 100 rpm in 900 ml aqueous buffer (ph 6.5) containing 0.05% w/w polysorbate 80 at 37° C. and the results are given below:

TABLE

| HOURS AFTER START OF TEST | % OF MORPHINE SULPHATE RELEASED |
| --- | --- |
| 1 | 6 |
| 2 | 11 |
| 4 | 21 |
| 8 | 37 |
| 12 | 48 |
| 16 | 57 |
| 24 | 67 |
| 30 | 72 |

We claim:

1. A process for the manufacture of a sustained release extrudate comprising the steps of:
    (a) mechanically working in a high-shear mixer, a mixture of a particulate drug and a particulate fusible carrier having a melting point from 35 to 150° C., the particulate fusible carrier selected from the group consisting of a hydrophobic fusible carrier, a hydrophilic fusible carrier and mixtures thereof, at a speed and energy input which allows said particulate fusible carrier to melt or soften whereby it forms agglomerates;
    (b) extruding said agglomerates to form an extrudate.

2. A process according to claim 1, wherein in step (b) said agglomerates are extruded through a plurality of orifices and then formed into pieces.

3. A process according to claim 2, wherein step (b) further comprises the step of continuing mechanically working said pieces to form sustained release particles.

4. A process according to claim 1, wherein during the mechanical working step, heat is supplied thereto by microwave energy.

5. A process according to claim 4, wherein only part of the heat is supplied by microwave energy.

6. A process according to claim 1, wherein said particulate drug is selected from the group consisting of morphine, tramadol, hydromorphone, oxycodone, diamorphine and pharmaceutically acceptable salts thereof.

7. A process according to claim 1, wherein said hydrophobic fusible carrier is selected from the group consisting of hydrogenated vegetable oil, hydrogenated castor oil, beeswax, carnauba wax, microcrystalline wax, glycerol monostearate and mixtures thereof.

8. A process according to claim 3, wherein said particulate fusible carrier is added stepwise during said continuing mechanically working step.

9. A solid dosage form obtainable by compressing particles obtained by the process of claim 3.

10. A capsule for oral dosing containing particles obtained by the process of claim 3.

11. A solid dosage form as set forth in claim 10, wherein said drug is unstable in water.

12. A solid dosage form as set forth in claim 10, wherein said drug is unstable in water.

13. The solid dosage form of claim 9, further comprising conventional tabletting excipients.

14. The capsule of claim 10, further comprising conventional capsuling excipients.

15. The process of claim 1, wherein said hydrophobic fusible carrier is a wax.

16. The solid dosage form of claim 9, wherein said hydrophobic fusible carrier is a wax.

17. The capsule of claim 10, wherein said hydrophobic fusible carrier is a wax.

18. The sustained release extrudate of claim 1, wherein release control component comprising a material selected from the group consisting of a water-soluble fusible material, a particulate organic material, a particulate organic material, a particulate organic material, a particulate inorganic material and mixtures thereof is included in the mixture of step (a).

19. A process according to claim 3, wherein said continuing mechanically working step further includes mechanically working the pieces with a hydrophobic fusible carrier, a hydrophilic fusible carrier or mixtures thereof.

20. A process according to claim 3, wherein said continuing mechanically working step is repeated one or more times.

21. A process according to claim 3, further comprising the step of repeating steps (b) and the continuing mechanically working step one or more times.

22. A solid dosage form formed by compressing pieces obtained by the process claim 2.

23. A capsule for oral dosing containing pieces obtained by the process of claim 2.

24. The process of claim 2, wherein said pieces provide sustained release of said drug.

25. A process according to claim 19, wherein said hydrophilic fusible carrier included in the continuing mechanically working step is selected from the group consisting of a polyethylene glycol having a molecular weight of from 1,000 to 20,000 g/m and a poloxamer.

* * * * *